US006520992B1

(12) United States Patent
Zollner et al.

(10) Patent No.: US 6,520,992 B1
(45) Date of Patent: Feb. 18, 2003

(54) UTILIZATION OF AN AUTOPOLYMERIZING ORGANOSILOXANE-BASED COMPOUND

(76) Inventors: Jan Zollner, Gartewfeldstrasse 18, D-65307 Bad Schwalbach (DE); Peer Eysel, Ronneburgblick 6, D-63505 Langenselbold (DE)

( * ) Notice: Subject to any disclaimer, the term of this patent is extended or adjusted under 35 U.S.C. 154(b) by 0 days.

(21) Appl. No.: 09/673,865

(22) PCT Filed: Apr. 21, 1999

(86) PCT No.: PCT/DE99/01215
§ 371 (c)(1),
(2), (4) Date: Nov. 16, 2000

(87) PCT Pub. No.: WO99/53970
PCT Pub. Date: Oct. 28, 1999

(30) Foreign Application Priority Data

Apr. 22, 1998 (DE) ......................... 198 17 698

(51) Int. Cl.⁷ .................................. A61F 2/44
(52) U.S. Cl. .................. 623/17.16; 623/901; 606/61
(58) Field of Search ............... 623/17.16, 901; 606/61

(56) References Cited

U.S. PATENT DOCUMENTS

| 4,558,109 A | * | 12/1985 | McAfee | 528/15 |
|---|---|---|---|---|
| 4,863,477 A | * | 9/1989 | Monson | 623/17 |
| 5,171,281 A | | 12/1992 | Parsons et al. | |
| 5,246,458 A | * | 9/1993 | Graham | 623/17 |
| 5,258,043 A | * | 11/1993 | Stone | 623/66 |
| 5,702,450 A | * | 12/1997 | Bisserie | 623/17 |
| 5,716,416 A | * | 2/1998 | Lin | 623/17 |
| 6,187,048 B1 | * | 2/2001 | Milner et al. | 623/17.12 |
| 6,240,926 B1 | * | 6/2001 | Chin Gan et al. | 623/11 |
| 6,428,576 B1 | * | 8/2002 | Haldimann | 623/17.16 |

FOREIGN PATENT DOCUMENTS

| DE | 2203242 | * | 3/1975 |
| DE | 234 609 | | 4/1986 |
| DE | 28 56 712 | | 10/1989 |
| DE | 39 11 610 | | 10/1990 |
| DE | 91 90 192 | | 9/1993 |
| EP | 0 176 729 | | 7/1989 |

OTHER PUBLICATIONS

Kirk–Othmer : Encyclopedia of Chemical Technology, vol. 20. 1982, pp. 943–947.*

* cited by examiner

Primary Examiner—Margaret G. Moore
(74) Attorney, Agent, or Firm—Paul & Paul

(57) ABSTRACT

The invention relates to a liquid or pasty organosiloxane based composition autopolymerizing into a permanently elastic silicon at ambient temperature. This composition is used for producing intervertebral disc implants that restore to a large extent the physiological range of movement of the intervertebral discs.

18 Claims, No Drawings

UTILIZATION OF AN AUTOPOLYMERIZING ORGANOSILOXANE-BASED COMPOUND

By his or her thirtieth year, the intervertebral discs in every human being exhibit degenerative changes. Disc prolapses necessitate surgical intervention; however, forays into the lumbar spine region can sometimes suffer from a high failure rate. The amount of recurrent intervertebral disc prolapse and Failed Back Surgery Syndrome or postnucleotomy syndrome is relatively high. After a nucleotomy, often following a problem-free interval. Increasing degeneration of the segment that has been operated upon and the degeneration of the bending joints are seen as the main source of long term deterioration. This means that one of the most important causes for complaint after intervertebral disc operations is the increased mobility of the vertebral motor segment. A possible solution is to stiffen the vertebral motor segment with the risk of increasing the load on the bordering segments and the danger of instability of the connectors. A further possibility is to implant an artificial intervertebral disc replacement, for example of a hydrophilic material packaged in a polyethylene net that is implanted in the dry condition.

Tests using a model of the spinal column have shown that a major cause of such long-term deterioration after intervertebral disc operations is the increased mobility of the vertebral motor segment. Thus the aim of the invention is to provide intervertebral disc implants that reproduce the physiological amount of movement of the disc as far as possible. The invention thus concerns the use of a fluid or pasty organosiloxane-based composition which is self-polymerisable at ambient temperature to a permanently elastic silicone for the production of intervertebral disc implants.

The disc consists of an outer zone, the anulus fibrosus, with the so-called Sharpey fibres and a gel-like parachondral inner zone, the nucleus pulposus. In accordance with the invention, the self-polymerisable organosiloxane-based composition is solely used for the production of nucleus pulposus implants, while the anulus fibrosus remains unaltered. Since the composition as used in the invention is fluid or pasty, after removing the gel-like inner zone from the anulus fibrosus, this composition can be introduced into the space thus formed and then undergoes self-polymerisation. On the one hand, then the anulus fibrosus acts to maintain the spacing of the vertebral segments, and on the other hand it simultaneously acts as a mould for the fluid or pasty composition of the invention, which is injected into this mould. A minimal endoscopic invasive entry to the intervertebral disc via the retroperitoneal space is sufficient from the ventral or, as is standard, dorsal direction. After removing the nucleus pulposus and introducing the hydrophobic organosiloxane-based composition of the invention, the anulus fibrosus can then be closed. The composition polymerises without additional heating to a permanently elastic silicone and completely fills the hollow space within the anulus fibrosus, providing a maximum surface area for load transfer, so that an even movement pattern is produced. Thus the invention means that the segmental stability of the so nucleotometrised intervertebral segment can be reinstated.

The organosiloxane-based composition as used in the invention must be sterile for use. Since such sterilisation usually cannot be carried out by the user of the fluid or pasty composition, the composition must be sterilised by the manufacturer and sold as internally sterile packages.

The biocompatibility of the compositions as used in the invention must be as high as possible in addition to having the highest possible continuous load capacity. It has been shown that on self-polymerisation, polydimethylsiloxane-based compositions produce silicones which possess both properties. Since the intervertebral disc is subjected to considerable pressure loads, this result was surprising and not predictable. The permanently elastic silicones produced from polydimethylsiloxanes have no deleterious effect on the surrounding tissue, on cell proliferation and on normal cell division. Degenerative changes were not observed. Linear polydimethylsiloxane-based compositions are particularly advantageous.

By copolymerising the methylsiloxane with differently substituted siloxanes, the reaction period for self-polymerisation and the properties of the silicone produced can be varied. As an example, instead of methyl groups, phenyl residues, ethyl groups or vinyl residues can be included, to produce mixed methylphenyl-, ethylmethyl- or methylvinyl-siloxanes, for example. Such co-polymerisates can have their substituents randomly arranged or arranged as a block copolymer. The end groups of the polydimethylsiloxane are preferably trimethylsiloxy groups, but at least a portion thereof can be silanol groups, vinyl groups or hydride groups. The viscosity of the linear polydimethylsiloxane can be governed by chain breaking groups, essential for the invention as for use, the compositions must be fluid or pasty.

In order to be self-polymerisable at ambient temperature, the compositions of the invention comprise a catalyst. Known siloxane catalysts are amines, such as aminopropylsilane derivatives, and lead, tin and zinc carbonic acid salts, also organic iron, cadmium, barium, antimony or zirconium salts. Tin octoate, laurate and oleate as well as dibutyltin salts are particularly suitable. The selected catalysts must be biologically compatible. These include addition catalysing noble metal complexes from group VIII, such as platinum, rhodium or ruthenium, which catalyse self-polymerisation within suitable polymerisation periods in very small amounts, for example concentrations as low as 1 to 2 ppm. In particular, platinum catalysts such as platinum-olefin complexes can catalyse addition of Si—H end groups to olefins such as vinyl functional siloxanes. Preferred compositions which polymerise to permanently elastic silicones are produced from mixtures of linear hydride functional polydimethylsiloxanes and linear vinyl functional polydimethylsiloxanes mixed with a suitable catalyst, in particular a platinum catalyst such as chloroplatinic acid or another platinum compound. In order to avoid premature polyaddition, such compositions are stored in two separate packs and are only combined immediately prior to use. Normally, the catalyst is stored together with the vinyl functional polydimethylsiloxane in one package and the hydride functional polydimethylsiloxane, optionally with the usual hardeners, if necessary with the addition of a vinyl functional polydimethylsiloxane but without the catalyst, is stored in the second package. The ratios of the amounts of both polydimethylsiloxanes used depends on the desired properties of the permanently elastic silicone.

Moisture from the air could also be used as the catalyst, however this is not important because the composition must be sterile for use in accordance with the invention.

The average molecular weight (number average) of the compositions of the invention is in the range 1000 to 150000, preferably in the range 50000 to 100000.

The compositions of the invention can also comprise the usual fillers such as finely divided silica such as fly ash, whereby the maximum particle size of such fillers should be 1 $\mu$m, for example in the range 0.01 to 0.5 $\mu$m. Other fillers which can be considered are dehydrated silica gels, diatomaceous earth, finely divided titanium dioxide, aluminium oxide or zirconium oxide. Finally, the usual process materials can be worked into the organosiloxane masses of the compositions of the invention, provided that they are biocompatible and do not affect the desired properties of the polymerised silicone, in particular its permanent elasticity and compression resistance.

What is claimed is:

1. A method for producing an intervertebral disc implant for improving the physiological amount of movement in an intervertebral disc damaged by degenerative changes, the method comprising:

removing the gel-like inner zone from the annulus fibrosus of the intervertebral disc to form a space, introducing a hydrophobic, noble metal catalyst selected from Group VIII containing self-polymerizable fluid or pasty organosiloxane-based composition into the space; and permitting at ambient temperature the composition to self-polymerize to a permanently elastic silicone which completely fills the hollow space within the annulus fibrosus.

2. A method according to claim 1, wherein the intervertebral disc implant is a nucleus pulposus implant.

3. A method according to claim 1, wherein the composition is based on dimethylsiloxane.

4. A method according to claim 1, wherein the composition includes a platinum catalyst.

5. A method according to claim 2, wherein the composition includes a platinum catalyst.

6. A method according to claim 3, wherein the composition includes a platinum catalyst.

7. A method according to claim 4, wherein the composition is based on hydride-functional siloxanes and vinyl-functional siloxanes.

8. A method according to claim 5, wherein the composition is based on hydride-functional siloxanes and vinyl-functional siloxanes.

9. A method according to claim 6, wherein the composition is based on hydride-functional siloxanes and vinyl functional siloxanes.

10. A method according to claim 2, further comprising sterilizing the composition.

11. A method according to claim 3, further comprising sterilizing the composition.

12. A method according to claim 4, further comprising sterilizing the composition.

13. A method according to claim 5, further comprising sterilizing the composition.

14. A method according to claim 6, further comprising sterilizing the composition.

15. A method according to claim 7, further comprising sterilizing the composition.

16. A method according to claim 8, further comprising sterilizing the composition.

17. A method according to claim 9, further comprising sterilizing the composition.

18. A method according to claim 1, wherein the composition is sterile.

* * * * *